United States Patent [19]

Henner et al.

[11] Patent Number: 4,912,046

[45] Date of Patent: Mar. 27, 1990

[54] PORTABLE INDUCIBLE CONTROL SYSTEM

[75] Inventors: Dennis J. Henner, Pacifica; Daniel G. Yansura, South San Francisco, both of Calif.

[73] Assignee: Genentech, Inc., South San Francisco, Calif.

[21] Appl. No.: 62,318

[22] Filed: Jun. 8, 1987

Related U.S. Application Data

[63] Continuation of Ser. No. 508,388, Jun. 27, 1983.

[51] Int. Cl.$^4$ .................. C12N 1/20; C12N 15/00
[52] U.S. Cl. ..................... 435/252.3; 435/252.31; 435/320; 935/29; 935/31; 935/40; 935/41; 935/72; 935/74
[58] Field of Search ............... 435/252.31, 172.3, 320, 435/252.3, 235; 935/29, 38, 39, 40, 41, 74

[56] References Cited

U.S. PATENT DOCUMENTS

| | | | |
|---|---|---|---|
| 4,374,927 | 2/1983 | Sninsky et al. | 435/68 |
| 4,430,434 | 2/1984 | Sanders et al. | 435/320 X |
| 4,506,013 | 3/1985 | Hershberger et al. | 435/172.3 |

FOREIGN PATENT DOCUMENTS

| | | | |
|---|---|---|---|
| 0036259 | 9/1981 | European Pat. Off. | 435/172.3 |
| 0063953 | 11/1982 | European Pat. Off. | 435/172.3 |
| 0067540 | 12/1982 | European Pat. Off. | 435/172.3 |
| 0184169 | 6/1986 | European Pat. Off. | |
| 8404755 | 12/1984 | World Int. Prop. O. | |

OTHER PUBLICATIONS

Deboer, H. A. et al., *Promoters, Structure and Function*, (Rodriguez, R & Chamberlin, M. Eds), pp. 462–481, (1982).
McLaughlin, Jr. et al., *Nuc Acids Res.*, vol. 10, (13) pp. 3905–3921, (1982).
Lee et al., *MolecGenGenet*, vol. 180, pp. 57–65, 1980.
Ehrlich, S. D., *Proc. Natl. Acad. Sci.*, vol. 75(3), pp. 1433–1436, 1978.
Bolivar, F. et al., *Gene*, vol. 2, pp. 95–113, 1977.
Russell et al., *Gene*, vol. 20, pp. 231–243, 1982.
Sninsky et al., *Gene*, vol. 16, pp. 275–286, 1981.
Hare et al., *Gene*, vol. 3, pp. 269–278, 1978.
Bethesda Research Labs, Inc. 1980 Catalog, pp. 48–49.
Donnelly et al., *Molecular Cloning and Gene Regulation in Bacilli* (Ganesan et al., Eds) Academic Press, pp. 63–72, 1982.
Williams et al. *Molecular Cloning and Gene Regulation in Bacilli* (Ganesan et al.) Academic Press, pp. 91–96, 1982.
Yansura, D. et al., *Proc. Natl. Acad. Sci.*, vol. 81, pp. 439–443, Jan. 1984.
Bogosian et al., *MolecGenGenet*, vol. 191, pp. 51–58, 1983.
Maniatis et al., *Cell*, vol. 5, pp. 109–113, 1975.
Wilcken-Bergmann et al., *Proc. Natl. Acad. Sci.*, vol. 79, p. 2427–2431, 1982.
Musso et al., *Proc. Natl. Acad. Sci.*, vol. 74, pp. 106–110, 1977.
Bennett et al., *J. Mol. Biol.*, vol. 121, pp. 113–137, 1978.
Gunsalus et al., *Proc. Natl. Acad. Sci.*, vol. 77, pp. 7117–7121, 1980.
Hu et al., Gene 62:301–313 (1988).
Brown et al., Cell 49:603–612 (1987).
Hu et al., Cell 48:555–566 (1987).
Davison et al., Gene 60:227–235 (1987).

*Primary Examiner*—Jayme A. Huleatt
*Attorney, Agent, or Firm*—Walter H. Dreger; Janet E. Hasak

[57] ABSTRACT

Shuttle vector systems are provided for the regulated expression of subject genes in transformed hosts. A promoter/operator which does not originate with the transformed host cell controls expression of the subject gene and a repressor, which also does not originate with the host cell, regulates the promoter/operator. According to this invention, promoter/operator—repressor functionalities from one bacterium are used in other bacteria, thereby obviating the need to locate homologous expression regulatory sequences for each bacterial host.

17 Claims, 12 Drawing Sheets pBS42 ↓

−IPTG

+IPTG

Fig. 8.

Pac-I

```
        EcoRI
        GAATTCGGTG GAAACGAGGT CATCATTTCC TTCCGAAAAA ACGGTTGCAT TTAAATCTTA CATATGTAAT
                    <<<< << lac Op >>>>>>      Sau3A                          *****    met
        ACTTTCAATT GTGAGCGGAT AACAATTCCG GATCAATCAA ATATTCAAAC GGAGGGAGAC GATTTTGATG
```

```
        EcoRI
        GAATTCTACA CAGCCCAGTC CAGACTATTC GGCACTGAAA TTATGGGTGA AGTGGTCAAG ACCTCACTAG
        GCACCTTAAA AATAGCGCAC CCTGAAGAAG ATTTATTTGA GGTAGCCCTT GCCTACCTAG CTTCCAAGAA
        AGATATCCTA ACAGCACAAG AGCGGAAAGA TGTTTTGTTC TACATCCAGA ACAACCTCTG CTAAAATTCC
        TGAAAAATTT TGCAAAAAGT TGTTGACTTT ATCTACAAGG TGTGGCATAA TGTGTGGAAT TGTGAGCGGA
              >>>>>>HindIII ****  *    XbaI EcoRI met                <<< <<< lac Op
        TAACAATTAA GCTTAAGGAG GTGTATCTAG AATTCATG
```

Spac-I

Fig. 12.

```
                                                                                GTGACCCACACC
                                                                                GGTGTGG
GGGAAGCTCACCTGGGTGCCCAACGGTGCACCGGTTTCTGCACTTGACAACACAACCAAC
CCCTTCGAGTGGACCCACGGTTGCCACGTGGCCAAAGACGTGAACTGTTGTTGGTTG

CCCACTGCATACCACAAGAGACCGCTGACTCGACTGGCTCTCCCATACACCGGCCACAC
GGGTGACGTATGGTGTTCTCTGGCACTGAGCTGACCGAGAGGGTATGTGGCGCGGGTGTG

CGCGTGTTGGCCACGACGTACACTGGTACAACAACCTACACTACCAGTGCACGTAGAGGA
GCGCACAACCGGTGCTGCATGTGACCATGTTGTTGGATGTGATGGTCACGTGCATCTCCT

GATTTGGTCCATTTGGCGGCAGCACACGCTCGGCACTTGCCGACGTCGTTCAACTTTGGT
CTAAACCAGGTAAACCGCCGTCGTGTGCGAGCCGTGAACGGCTGCAGCAAGTTGAAACCA

GCAGTTAAAGCAGAAAAAGTCACTGAGCTGCTGGTGCGCATGAAGCGTGCAGAACTCTAT
CGTCAATTTCGTCTTTTCAGTGACTCGACGACCACGCTACTTCGCACGTCTTGAGATA

TGCCCCAGGCCGATTCCTCCGATTCGGCCAACGGGCGACAGACACAAGCAATCGTTTATC
ACGGGGTCCGGCTAAGGAGGCTAAGCCGGTTGCCCGCTGTCTGTGTTCGTTAGCAAATAG

G
CTTAA
```

PORTABLE INDUCIBLE CONTROL SYSTEM

This is a continuation, of application Serial No. 06/508,388 filed June 27, 1983, now abandoned.

BACKGROUND

This invention relates to the field of producing foreign proteins in host bacteria using recombinant techniques. More specifically, the invention relates to novel control sequences which regulate the expression of a desired gene and thus to production of its encoded protein in response to factors under the control of the experimenter. The invention is applicable to a wide range of prokaryotic hosts.

It is now understood quite clearly that there is more to the successful use of recombinant techniques to produce desired proteins than merely inserting the appropriate gene into an expression vector and transforming a suitable host. Not only must the expression system be recognized by the host cell, but the timing of the expression must be regulated to insure that the protein is produced at high levels only when the cell can best tolerate the amounts of foreign protein. Foreign protein genes are often expressed at levels that produce protein in much greater amounts than those of any endogenous protein. If such large amounts of protein are the goal, they may be lethal, and expression is often best separated from growth phase. Alternatively, it may be desirable to regulate the specific level of protein production so as to optimize its functionality in the context of other cellular events. Accordingly, workers in this field have employed promoters which are susceptible to control by repressor binding to operator sequences either contained within the promoter sequence or slightly downstream.

Microorganisms themselves utilize several control mechanisms for regulating the level of protein production. In some organisms and for some proteins, control is exerted at the translational level by direct inhibition or stimulation of the rate of protein synthesis at the ribosome or by stabilization or destabilization of mRNA. This translational approach at present does not easily lend itself to fine-tuned voluntary control by the experimenter, and has not been used to obtain the desired objectives of recombinant technology such as high levels of protein production. At least two control strategies have been described which are used by microorganisms at the level of transcription. One involves "sigma factors" which are produced by microorganisms at various stages of their life cycles, and which bind to RNA polymerase to render it more, or less, suitable for particular promoter sites in the DNA sequences to be transcribed. This method, like translational control, is not presently employed as a means to effect external control of expression, because it does not permit the desired level of controllability.

A second transcriptional strategy employs an "operator"—i.e., a sequence in the operon proximal to the promoter either included within the promoter itself or somewhat downstream, to which a repressor molecule is bound when the transcription is to be shut off. The repressor is removed from the operator in response to a depletion in its total effective amount, often obtained by supplying to the cell an inductor which inactivates the repressor protein. It is this strategy which has been co-opted by biotechnologists to effect their own control over expression. For example, see Sninsky, J. J., et al., *Gene*, 16: 275 (1981). However, heretofore, this approach has been available only in *E. coli* and closely related gram negative hosts, since it is only in these systems that the operator/repressor mechanism has been described. Furthermore, such control systems have not been constructed in a form so that they can function in conjunction with any desired gene for expression in other hosts besides the natural host for the control system. The ability to so function renders the system "portable."

The present invention provides a portable control system which comprises a promoter/operator sequence wherein the operator is potentially under the control of a repressor, plus the coding sequence for this repressor also operably linked to a suitable promoter. Such a compilation of sequences can be utilized in a large variety of hosts including hosts which are not known to employ such control systems endogenously. Thus a control system is provided which can be inserted into plasmid vectors or into the genome of the desired host organism so as to provide an inducible transcription control for a gene sequence operably linked to it. This is a suitable regulation system for genes encoding desired proteins which is easily manipulated and controlled, both in traditional *E. coli* hosts and more importantly, in less traditional, gram positive hosts. These latter hosts within their own complement of genetic and plasmid material either lack this system of controlling gene expression altogether or such systems of regulation are not yet known to be associated with them.

SUMMARY OF THE INVENTION

The present invention relates to a portable bacterial transcription control system for expression of a desired coding sequence. It is basically a promoter/operator/repressor set which is usable for expression of the coding sequence. It comprises an operator DNA sequence capable of binding a repressor and a DNA sequence encoding a repressor compatible with this operator; the operator, repressor encoding sequence, and desired gene sequence are each operably linked to one or more promoters. The result is a transcriptional control system which is regulatable by induction, and which is generally applicable to host bacterial strains, including gram positives. Also included in the invention are methods for regulating the expression of a desired gene by using the aforementioned systems, and to expression vectors containing such systems. The invention also relates to bacteria and to bacterial cultures transformed with these vectors.

In still another aspect, the invention relates to a hybrid promoter/operator comprising the sequence of the RNA polymerase recognition site for the penicillinase promoter and the operator region of the β-galactosidase (lac) promoter/operator, and a similar hybrid promoter comprising the sequence of the RNA polymerase recognition site of an SPO-1 phage promoter and the operator region of the lac promoter/operator. These hybrids are particularly effective as targets for repressor control in the method of the invention.

It is surprising for several reasons, in the context of present knowledge, that the control system of the invention is workable in a variety of hosts. It is known that the lacI repressor functions as a multimer in its usual *E. coli* milieu; it is uncertain whether the cellular environment of other organisms would permit the correct conformational arrangement so as to permit aggregation. Furthermore, the RNA polymerases of noncoliform hosts may be sufficiently different from that of *E. coli* to render the operator/repressor aggregation ineffective in inhibiting the polymerase. Finally, with respect to gram positives, it is unclear as to whether suitable induces would be able to permeate into the cell to enable contact with repressor.

BRIEF DESCRIPTION OF THE DRAWINGS

FIG. 8 gives the entire nucleotide sequence for each of the pac-1 and spac-1 hybrid promoter/operators.

FIG. 12 shows the sequence of a fragment containing an Eco RI and a BstE II site used in the construction of pIQ45.

DETAILED DESCRIPTION

A. Definitions

Figure 1:
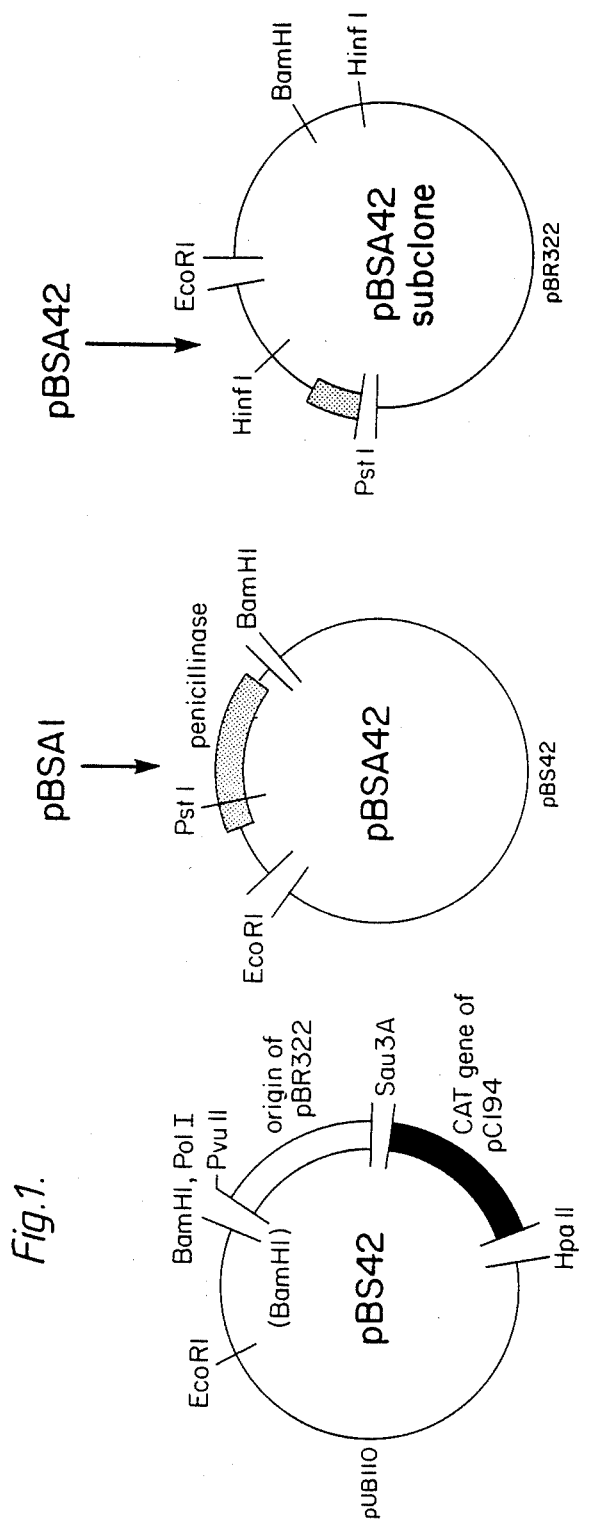
FIG. 1 shows the construction of the shuttle vectors pBS42, pBSA42, and a pBSA42 subclone.

As used herein, DNA sequences which are "operably linked" refer to DNA sequences which are juxtaposed in such a way that their respective functions are mutually dependent. For example, a promoter operably linked to a coding sequence is capable of effecting the expression of the coding sequence. An operator which is operably linked to a promoter is capable, when bound to a repressor protein, of inhibiting the function of the promoter, and when derepressed of permitting it to function normally. Such an operator sequence may overlap the promoter sequence or may lie downstream from it; "operably linked" is independent of such location as long as the functional interrelationship between the two sequences is maintained.

"Compatible repressor" means a protein which is capable of binding an operator sequence (to which it is compatible) whereby the operator is effective in inhibiting the promoter to which the operator is "operably linked". Thus, a "compatible" repressor has meaning only when referred to a related operator sequence.

"Inducible" promoter which can be "turned on" by derepression in response to simple manipulations such as temperature shifts or addition of compounds to the medium harboring the organisms containing the promoter system, thus providing a voluntary system of expression. A typical example of such an "inducible" control system is placUV5 which contains a downstream operator sequence inducible by removing the "lac repressor". Such removal can be induced by adding isopropyl-$\beta$-D-thiogalactoside (IPTG) to the medium; the inducer permeates the cells, binds to repressor protein and thus permits expression of the $\beta$-galactosidase gene in untransformed cells or, in cells transformed by recombinant expression vectors, of whatever gene is placed in control of the placUV5 promoter. This system is described in detail in U.S. patent application No. 338,397 filed Jan. 11, 1982, issued as U.S. Pat. No. 4,551,433 on Nov. 5, 1985, which is a continuation-in-part of U.S. Ser. No. 328,174, filed Dec. 7, 1981, which in turn is a continuation-in-part of U.S. Ser. No. 264,306 filed May 18, 1981, both U.S. Ser. No. 328,174 and 264,306 being abandoned, and published in EPO publication No. 0067540, Dec. 22, 1982. Another commonly used promoter, whose inducibility is, however, less sensitive to additions to the medium, is the trp promoter, disclosed in pending U.S. Application Ser. No. 07/076,253 filed July 21, 1987, which is a continuation of U.S. Application Ser. No. 685,521, filed Dec. 24, 1984, now abandoned, which is a continuation of U.S. Ser. No. 307,473, filed Oct. 1, 1981, now abandoned, which in turn is a continuation of U.S. Ser. No. 133,296 filed mar. 24, 1980, now abandoned and published in EPO publication No. 0036776. This promoter is inducible by addition of indole acrylic acid (IAA) to the culture medium. The inducer binds competitively with tryptophan to the repressor protein, but is less finely tuned to voluntary control than the aforementioned lac promoter because a minimal level of derepression is mandated by the required presence of tryptophan needed for protein synthesis.

"Portable" control system means that the system is capable of being ligated operably to a desired gene sequence, and capable of controlling expression in prokaryotic hosts in general—not just in the prokaryotic host of its origin. Such potential hosts include bacteria spanning the entire taxonomic scope of prokaryotes.

"Gram positive" bacteria refers to the standard definition for such bacteria wherein a single membrane envelope which permits active transport of substances into and out of the cell encloses the bacterium. Rigidity is supplied by a cell wall which is capable only of passive permeation. This class of organisms is important to the present invention because heretofore it has not been possible to provide inducible transcriptional controls in such organisms. The portable control systems of the present invention are, however, capable of providing such control.

On the other hand, *E. coli,* as representative of gram negative organisms—i.e., those which contain two enveloping membranes capable of active transport, are the traditional hosts for control systems analogous to those described above. Distantly related gram negative strains such as Pseudomonas are not known to possess such systems. Of course, a major advantage of the portable systems of the present invention ia that they are useable in a wide variety of hosts. This does not mean, however, that they are inapplicable to the more commonly employed host systems such as *E. coli.*

B. GENERAL DESCRIPTION

The control system of the present invention employs recombinant techniques to splice together a promoter/operator and the gene (under suitable promoter regulation) encoding the compatible repressor which binds to the operator of the promoter/operator sequence. This package is then placed in operable functionality with a desired gene sequence. The control package therefore provides not only the promoter/operator under which the desired gene is to function, but also provides the expression system for the control mechanism, i.e., the repressor. While such provision is not mandatory for organisms such as *E. coli,* which contain genes capable of expressing repressor protein in their own genomes, it is a requisite part of the sequence where the host is to be an organism which does not encode the repressor.

A practical approach to the construction of the control system operably linked to DNA encoding a desired protein results in a tandem construction. The desired gene is placed under the control of a promoter/operator, preferably a hybrid promoter/operator. The possibility of employing a hybrid promoter/operator permits the promoter to be selected from those which are known to be effective in an intended host organism, and the operator to be chosen from among those which are known to be controlled by a repressor capable of being effected by a compound introduced extracellularly i.e. an inducible operator. Thus, in one preferred embodiment, the penicillinase promoter which is known to be functional in *B. subtilis* is combined with the lac operator which is repressed by a protein affected in turn by a commonly used inducer, IPTG. The promoter/operator thus has features which permit its use in noncoliform hosts while permitting traditional coliform systems of control to be used. Either ligated to, or cotransfected with, the constructed hybrid promoter/operator/desired gene operon is an additional operon comprising a promoter compatible with the host cell operably linked to the gene encoding the repressor compatible with the promoter/operator of the extreme operon. A suitable combination here for use in, for example, *B. subtilis* is the penicillinase promoter operably linked to the gene encoding lacI repressor; however, any promoter operable in the desired host may also be used. Those promoters most commonly used in recombinant DNA construction include the β-lactamase (penicillinase) and lactose promoter systems (Chang et al, *Nature,* 275: 615 (1978); Itakura, et al, *Science,* 198: 1056 (1977); (Goeddel, et al *Nature* 281: 544 (1979)) and a tryptophan (trp) promoter system (Goeddel, et al, *Nucleic Acids Res.,* 8: 4057 (1980); EPO Appl Publ No. 0036776). While these are the most commonly used, other microbial promoters have been discovered and utilized, and details concerning their nucleotide sequences have been published, enabling a skilled worker to ligate them functionally with plasmid vectors or hybridize them to suitable operator sequences (Siebenlist, et al, *Cell* 20: 269 (1980)).

Thus, the control system vector contains two complete operons, one a controllable operon for expression of the desired gene and the other permitting production of the control protein which is capable of repressing the promoter/operator which effects the desired gene expression.

In the preferred embodiments described hereinbelow, the desired gene sequences are the penicillinase gene of Bacillus and the gene encoding leukocyte interferon. Of course, by use of suitable recombinant techniques, any desired gene may be placed under the control of the system of the invention.

Further, the constructions, for convenience, contain all elements of the control system as well as the desired gene on the same expression vector. Such constructions are only one example of the manner in which the invention may be practiced. It is also possible in place, for example, the promoter/operator/desired gene system on one plasmid, and the repressor expression system on another, and to cotransform suitable hosts with both plasmids. Also, by using complementary sequences on the plasmids constructed to those found in the host genome, an enhanced integration of the plasmid sequences into the genome of the host may be effected. Accordingly, the control systems of the present invention may be found not only in portable vector constructions, but also integrated into the genetic material of the transformed host.

C. METHODS EMPLOYED

C.1 Vector Construction

Construction of suitable vectors containing the desired coding and control sequences employs standard ligation techniques. Isolated plasmids or DNA fragments are cleaved, tailored, and religated in the form desired to form the plasmids required. The methods employed are not dependent on the DNA source, or on the intended host.

Cleavage is performed by treating with restriction enzyme (or enzymes) in suitable buffer. In general, about 1 μg plasmid or DNA fragments is used with about 1 unit of enzyme in about 20 μl of buffer solution. (Appropriate buffers and substrate amounts for particular restriction enzymes are specified by the manufacturer.) Incubation times of about 1 hour at 37° C. are workable. After incubations, protein is removed by extraction with phenol and chloroform, and the nucleic acid is recovered from the aqueous fraction by precipitation with ethanol.

If blunt ends are required, the preparation is treated for 15 minutes at 15° with 10 units of *E. coli* DNA Polymerase I (Klenow), phenol-chloroform extracted, and ethanol precipitated.

Size separation of the cleaved fragments is performed using 6 percent polyacrylamide gel described by Goeddel, D., et al, *Nucleic Acids Res.,* 8: 4057 (1980) incorporated herein by reference.

For ligation, approximately equimolar amounts of the desired components, suitably end tailored to provide correct matching, are treated with about 10 units T4 DNA ligase per 0.5 μg DNA. (When cleaved vectors are used as components, it may be useful to prevent religation of the cleaved vector by pretreatment with bacterial alkaline phosphatase.)

In the examples described below correct ligations for plasmid construction are confirmed by transforming *E. coli* K12 strain 294 (ATCC 31446) with the ligation mixture or other suitable microorganisms such as *B. subtilis,* strain 1168. Other *E. coli* strains used for the constructions were D1210 (Sadler, J. R. et al 1980 Gene 8: 279), which was used for the construction of plasmids containing hybrid promoters, and strain 3300 (*E. coli* Genetic Stock Center No. 808), which was used for the construction of pIQ45.

Successful transformants were selected by ampicillin, tetracycline, chloramphenicol or neomycin resistance depending on the mode of plasmid construction. Plasmids from the transformants were then prepared, analyzed by restriction and/or sequenced by the method of Messing, et al, *Nucleic Acids Res.,* 9: 309 (1981) or by the method of Maxam, et al, *Methods in Enzymology*, 65: 499 (1980).

A commonly used technique for obtaining a DNA sequence cleaved at a specific location, which is used frequently in the invention, is the "primer repair" reaction described in U.S. No. 133,296, filed Mar. 4, 1980, now abandoned, incorporated by reference, and published as EPO Application Publication No. 0036776 Sept. 30, 1981. In this reaction, the fragment of DNA desired to be specifically cleaved is denatured and mixed with a primer approximately 12 bases long, which is complementary to one of the denatured strands. The primer is constructed so that one end of the primer is exactly contiguous with the desired cleavage point. The primary can be designed so as to be complementary either to the sense or anti-sense strand, thereby controlling the direction of "repair". In the repair, the mixture is treated with DNA polymerase I (Klenow fragment) which effects the synthesis of a strand complementary to the denatured, primer-bound. DNA in the 5' or 3' direction starting at the 3' end of bound primer, and cleaving back the remaining single stranded denatured portion extending from the primer's 5' end.

C.2. Transformation

Cell transformation of *E. coli* was accomplished by the CaCl$_2$ treatment of Cohen, F. N. et al., *Proc. Natl. Acad. Sci.* (USA), 69: 2110 (1972). Transformation of *B. subtilis* employed the method of Anagnostopoulos, C., et al., *J. Bacteriol.*, 81: 741 (1961). Selection for successful transformants using the plasmids of the present invention was conducted by suitable concentrations of the appropriate antibiotic: 12.5 μg/ml chloramphenicol (CMP), 20 μg/ml neomycin (NEO), 20 μg/ml ampicillin (AMP), 5 μg/ml erythromycin (ERY), and 3 μg/ml tetracycline (TET).

C.3. Assays

Penicillinase is assayed (including detection of activity on polyvinylalcohol (PVA) plates) by the method of Sherratt, D. J. et al., *J. Gen. Microbiol.*, 76: 217 (1973). Leukocyte interferon assays were performed by growing *B. subtilis* strain I168 that had been transformed with the described plasmids in L broth supplemented with 10 μg/ml NED and 0.5 percent glucose at 37° C. until the cells attained a density at OD 600 of 1.0. Triplicate one ml aliquots were harvested by centrifugation in an Eppendorf microfuge for 4 min. The pellets were suspended in 0.1 ml of a solution of 10 mg/ml lysozyme in 10 mM Tris, 1 mM EDTA, pH 8 and incubated at 37° C. for 15 min. 0.9 ml of 0.1 percent SDS was then added and the cells were diluted 50–300 fold in phosphate buffered saline containing 1 mg/ml bovine serum albumin. Interferon levels were determined by the cytopathic effect inhibition assay using viscular stomatitis virus on MDBK cells as described by Stewart, W. E. *The Interferon System*, Springer, Berlin (1979).

D. DETAILED DESCRIPTION OF PREFERRED EMBODIMENTS

D.1. Controlled Expression of *B. licheniformis* penicillinase

D.1.1 Construction of the Expression Vector

The plasmid pAIQ25 contains the penicillinase gene operably linked to the control system of the present invention. In this construction, the penicillinase gene is preceded by a hybrid promoter/operator comprising a portion of the penicillinase promoter and the lac operator. Downstream from the penicillinase gene is the coding sequence for the lacI repressor protein under the control of the penicillinase promoter. The backbone portions of this plasmid contain an origin of replication operable in Bacillus.

Figure 4:
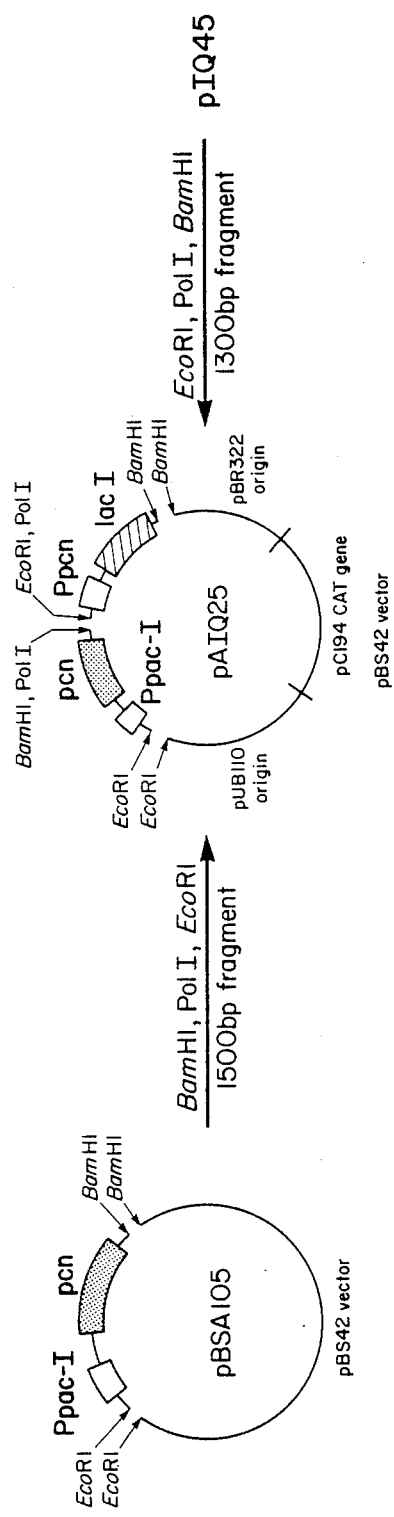
FIG. 4 shows the construction of pAIQ25, an expression vector for penicillinase under control of the portable system of the invention.

This plasmid is constructed by ligation of three fragments (see FIG. 4). Fragment 1 is a 1500 base pair EcoRI-blunt ended fragment derived from an intermediate plasmid pBSA105, which contains the hybrid (pac-1) promoter operably linked to the penicillinase gene. Fragment 2 is a 1300 base pair blunt ended-BamH1 fragment derived from intermediate plasmid pIQ45 which contains the lacI gene under the control of the penicillinase promoter. Fragment 3 is an EcoR1-BamH1 backbone fragment derived from pBS42. Construction of the three fragments used in this ligation is described below.

D.1.2 Construction of Fragment 1—Penicillinase Operon Containing the Pac-1 Promoter/Operator Fragment 1, containing the pac-1 promoter/operator and the penicillinase gene is derived from an intermediate plasmid pBSA105 by treating first with BamH1, filling in using the Klenow fragment of DNA polymerase, followed by digestion with EcoR1. pBSA105 is constructed as follows: In step 1 the penicillinase gene is inserted into the pBS42 vector described in paragraph D.1.4 below to give pBSA42 (see FIG. 1). The penicillinase gene *Bacillus licheniformis* strain-749/C (ATCC 25972) was isolated by the method of Imanaka, T. et al., *J. Bacteriol.* 147: 776 (1981). The vector plasmid used in the isolation of the penicillinase gene was pBS7, which is described in paragraph D.3.1. The pBS7 derivative carrying the penicillinase gene was designated pBSA1.

Step 1 was accomplished by opening pBS42 by double digestion with EcoR1 and BamH1, and religating in the presence of the entire penicillinase gene which had been modified by converting a HpaII site 40 base pairs upstream of the promoter into an EcoR1 site, and the PvuII site 600 base pairs downstream from the 3' end of the gene to a BamH1 site. These conversions employed standard techniques. The resultant pBSA42 plasmid then contains the entire penicillinase gene inserted into a pBS42 backbone. A subclone of pBSA42 (pBSA subclone) was constructed by ligating the EcoRI-PstI fragment of pBSA42 containing the penicillinse promoter into an EcoRI-PstI digested pBR322 vector (FIG. 1). pBSA42 or its subclone provided the three fragments, A, B, and C which were ligated to provide pBSA105.

Figure 2:
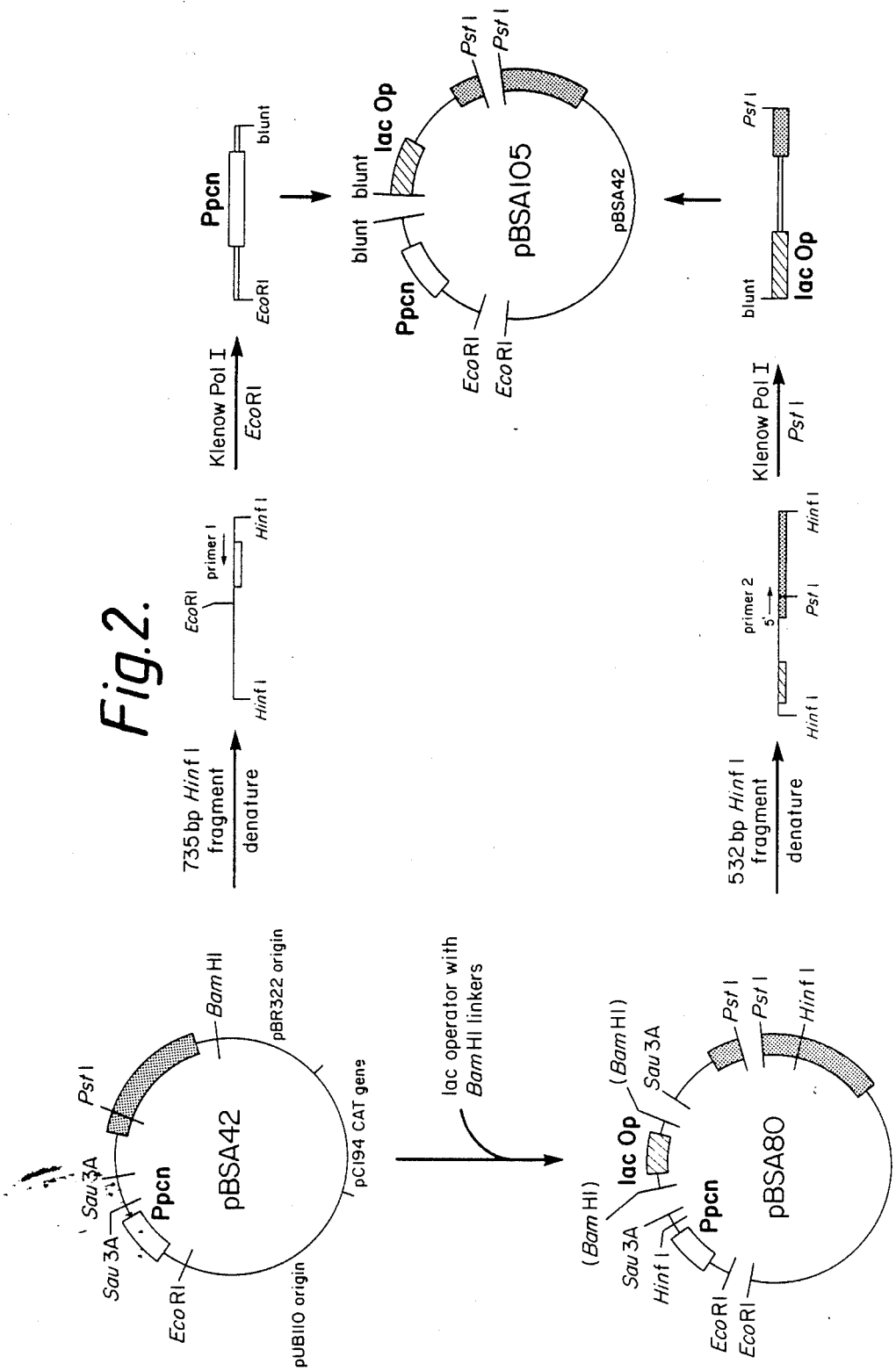
FIG. 2 shows the construction of the plasmid pBSA105 which contains the penicillinase gene under the control of the pac-1 promoter operator.

Fragment A is the product of double digestion of pBSA42 with EcoR1 and PstI as shown in FIG. 2. This provides the backbone portion of pBSA42 along with the C-terminal portion of the penicillinase gene.

Fragment B contained a modified penicillinase promoter and is derived from a subclone of pBSA42 by HinfI cleavage. As shown in FIG. 2, digestion of the pBSA42 subclone with HinfI provides a 730 base pair fragment which contains the penicillinase promoter (as well as a portion of the gene). The HinfI cleavage fragment is then denatured and subjected to a primer repair reaction so as to cut back to position -4 in the penicillinase promoter. The primer used is 5'-GAAAGTAT-TAC-3' which binds to the DNA beginning at approximately -4 reading from the 3' direction. The resulting blunt ended fragment is further cleaved at the EcoR1 site upstream from the promoter. The resulting fragment B thus contains that portion of the penicillinase promoter which is upstream of position -4.

Fragment C contains the lac operator and the N-terminal portion of the penicillinase gene. To form fragment C, an intermediate plasmid pbSA80 is constructed from pBSA42 by insertion of the lac operator. PBSA42 was digested with Sau3A which deletes an 80 base pair fragment between the promoter and ribosome binding site. A synthetic DNA sequence containing the lac operator bounded by BamH1 sites, i.e., having the sequence

```
5'-GATCCGGTGTGGAATTGTGAGC-
   GGATAACAATTCCGGCCACACCT-
   TAACACTCGCCTATTGTTAAGGCCTAG-
   5'
``` was then inserted by ligation into the remaining Sau3A sites, to give pBSA80.

This intermediate plasmid pBSA80 was then treated to form fragment C. Treatment with HinfI yields a 532 base pair fragment which contains the penicilinase ribosome binding site, the entire lac operator, and the N terminal portion of the penicillinase gene. A primer repair reaction of this fragment serves to remove the RNA polymerase binding site. The primer used was 5'-AATTGTGAGCGG-3' which binds at the immediate 5' end of the lac operator in this construction. The resulting shortened fragment was further cleaved with PstI to obtain the shortened N-terminal portion of the gene. Fragment C contains part of the hybrid pac-1 promoter/operator. The sequence of this promoter/operator is shown in FIG. 8.

Fragments A, B, and C were then ligated to provide the desired plasmid pBSA105. This plasmid contains the hybrid pac-1 promoter/operator which includes a portion of the penicillinase promoter and the lac operator both upstream from the penicillinase ribosome binding site and penicillinase gene.

D.1.3 Construction of Fragment 2 Containing the LacI Repressor Gene under Control of the Penicillinase Promoter Fragment 2 is the 1300 base pair fragment derived from pIQ45 by digestion with EcoR1, blunt ending with DNA polymerase, and followed by treatment with BamH1. pIQ45 is constructed of fragments from a subclone of pBSA42 as described above, and pHiQ6, described in Hare, D. L. et al, Gene, 3: 269 (1978). pHiQ6 contains the entire lacI gene.

Figure 3:
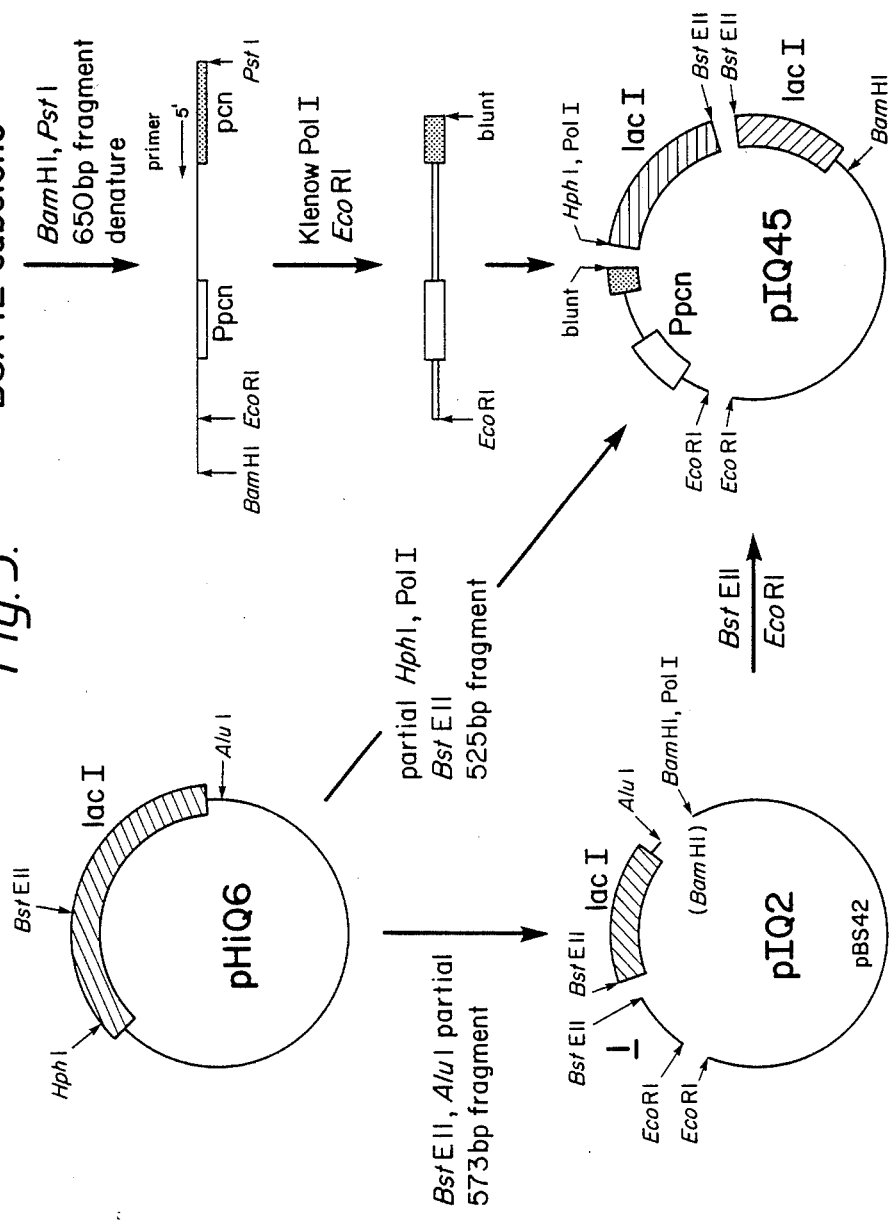
FIG. 3 shows the construction of the plasmid pIQ45, an expression vector for the lacI repressor.

In the three way ligation which forms pIQ45, fragment D is derived from pBSA42 and contains the penicillinase promoter and the first two amino acids of the penicillinase gene. Since the first two amino acids of the penicillinase gene are identical to the first two amino acids of the lacI gene, fragment D can be used in the reconstruction of the lacI gene coding sequence. To construct fragment D, the pBSA42 subclone is digested with BamH1 and Pst1 to provide a 650 base pair fragment containing the penicillinase promoter and the N-terminal portion of the penicillinase gene. The gene is shortened to include only the codons for the first two amino acids by a primary repair reaction using as primer against the denatured negative sense strand of this fragment, 5'-TTTCATCAAAA-3'. The resulting abbreviated fragment was further cleaved with EcoR1 to give fragment D as shown in FIG. 3.

Fragments E and F are ultimately derivable from pHiQ6 as follows: Fragment E is formed by a partial digestion of pHiQ6 with Hph1, blunt ending with the polymerase 1, followed by treating with BstEII and isolating the 525 base pair fragment which contains the N-terminal portion of the lacI gene beginning at amino acid number 3. Thus, fragments D and E together will supply the promoter and the N-terminal portion of the gene preceding the BstE1II site.

The remaining portion of the gene and the backbone portion of pIQ45 are supplied by fragment F. Fragment F is derived from pHiQ6 through an intermediate plasmid, pIQ2, which includes the backbone portion of pBS42. This plasmid is formed by a three-way ligation between a BstEII-partial Alu 1 double digestion of pHiQ6 (see FIG. 3), the EcoR1 filled-in BamHI fragment from pBS 42 (see FIG. 1) and a fragment containing an EcoR1 and BstEII site which has the base sequence shown in FIG. 12. Ligation of these three fragments results in pIQ2, which contains the pBS42 backbone and the portion of the lacI gene extending from the BstEII site to the C terminus. Cleavage of pIQ2 with BstEII and Ecor1 provides fragment F.

The plasmid pIQ45 resulting from ligation of fragments D, E, and F therefore contains the penicillinase promoter linked to the entire lacI gene sequence.

D.1.4 Construction of Fragment 3-Backbone Segment

Fragment 3 is the vector portion of pBS42 double digested with EcoR1 and BamH1. pBS42 is formed by three way ligation of fragments derived from puB110, pC194, and pBR322 (see FIG. 1). The fragment from pUB110 is the approximately 2600 base pair fragment between the HpaII site at 1900 and the BamH1 site at 4500 and contains an origin of replication operable in Bacillus: Grycztan, T. J. et al., *J. Bacteriol.*, 134: 318 (1978); Jalanko, A. et al., *Gene*, 14: 325 (1981). The BamHI site was blunt ended by filling in using DNA polymerase I. The pBR322 portion is the ~1100 base pair fragment between the PvuII site at 2067 and the Sau3A site at 3212 which contains the *E. coli* origin of replication: Bolivar, F. et al., *Gene* 2: 95 (1977); Sutcliffe, J. G., *Cold Spring Harbor Symposium* 43: I, 77 (1978). The pC194 fragment is the ~1200 base pair fragment between the HpaII site at 973 and the Sau3A site at 2006 which contains the gene for chloramphenicol resistance expressible in both *E. coli* and *B. subtilis*. Ehrlich, S. D., *Proc. Natl. Acad. Sci.* (USA), 74: 1680 (1977); Horynuchi, S., et al., *J. Bacteriol.* 150: 815 (1982).

The resulting plasmid pBS42 thus contains origins of replication operable both in *E. coli* and in Bacillus and an expressible gene for chloramphenicol resistance. Since the ligation recreates the BamH1 site derived from pUB110, double digestion of pBS42 with EcoR1 and BamH1 provides subsubstantially the entire plasmid.

D.1.5 Expression of the Penicillinase Gene.

Figure 5:
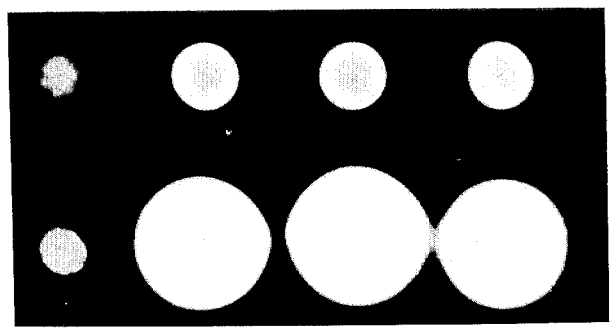
FIG. 5 shows detection of penicillinase expression in IPTG induced cells grown on PVA plates.

The ligation mixture containing pAIQ25 (see D.1.1) was transformed into *Bacillus subtilis*, strain Bacillus Genetic Stock Center, Columbia, Ohio, No. 1A1 (ATCC No. 27689) and successful transformants were selected by chloramphenicol resistance. Several of these were picked to replicate on PVA indicator plates (see paragraph C.3), with and without 1 mM IPTG. The results, shown in FIG. 5, indicate that production of penicillinase was enhanced in the presence of IPTG. Representative colonies were grown overnight in LB +0.5 percent glucose and 10 µg/ml chloramphenicol with and without 1 mM IPTG. Appropriate dilutions of the cell broth in 0.1M sodium phosphate buffer (pH 7.0) were assayed for penicillinase by the method of Sherratt et al. (supra at C.3). Cell grown in the presence of IPTG showed penicillinase levels at an average of 6,000 units/ml of cell broth while those grown in the absence of IPTG produced only 60 units/ml of culture. Further, the supernatant fraction of these cultures when subjected to SDS-PAGE showed a band of 33,000 molecular weight (the approximate MW of penicillinase) only in cultures induced by IPTG (FIG. 6).

Figure 6:
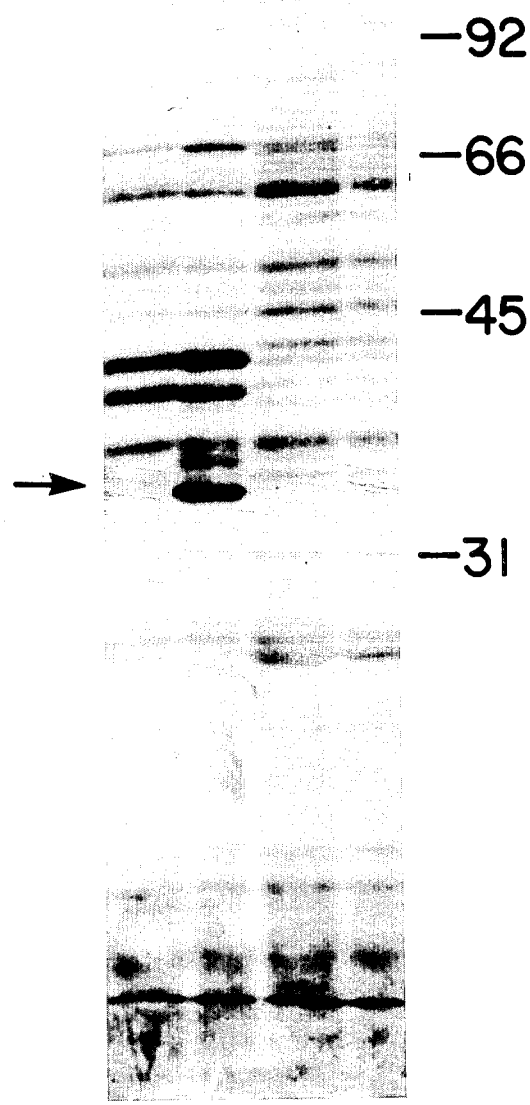
FIG. 6 shows the results of SDS PAGE on supernatants derived from Bacillus cultures transformed with pAIQ25.

In FIG. 6 Lane 1 shows I168 transformed with pAIQ25, grown without IPTG and Lane 2, I168 transformed with pAIQ25, grown with IPTG, Lanes 3 and 4, I168 transformed with pBS42, grown with and without IPTG.

D.2 Construction of the spac-I promoter

The entire sequence of the spac-I hybrid promoter is shown along with that of the pac-I hybrid in FIG. 8. The sequence that is not underlined corresponds to the natural sequence of the SPO-1 promoter; the underlined sequence corresponds to the lac operator (designated on the figure) and a Shine-Dalgarno sequence (designated with *'s).

The spac-I promoter is similar to the pac-I promoter whose construction is described in D.1.2 above, except that the RNA polymerase recognition site is derived from a B. subtilis phage promoter, the sequence of which is known to correspond to that which lies on the EcoR1* fragment 26 of SPO-1 DNA as described by Lee, G. et al., Mol. Gen. Genet. 180: 57 (1980). SPO-1 DNA was prepared as described by Lee, G., et al. (supra) and EcoR1* fragment 26 was prepared by digestion of the SPO-1 DNA with 10 U/ug in 10 percent glycerol, 0.025M Tris-HCl pH 8.5, and 0.002 $\mu$gC12, fractionation on a 5 percent acrylamide gel, and electroelution of the 1.1 kbp fragment 26. The previous reported sequence showed that a HindII site cut within the -35 portion of the RNA polymerase recognition site and the 232 bp fragment containing a part of the -35 sequence and the 5' "upstream" region was isolated. Synthetic DNA which recreated the remainder of the RNA polymerase recognition site was ligated onto the 232 bp fragment. This sequence extended to the end of the -10 portion of the recognition site. Further synthetic DNA which contained the lac operator and a Shine-Dalgarno sequence (or ribosome binding site) was ligated to the recreated RNA polymerase recognition site.

D.3 Controlled Expression of the Leukocyte Interferon A Gene.

D.3.1 Construction of pLIQ1

Figure 7:
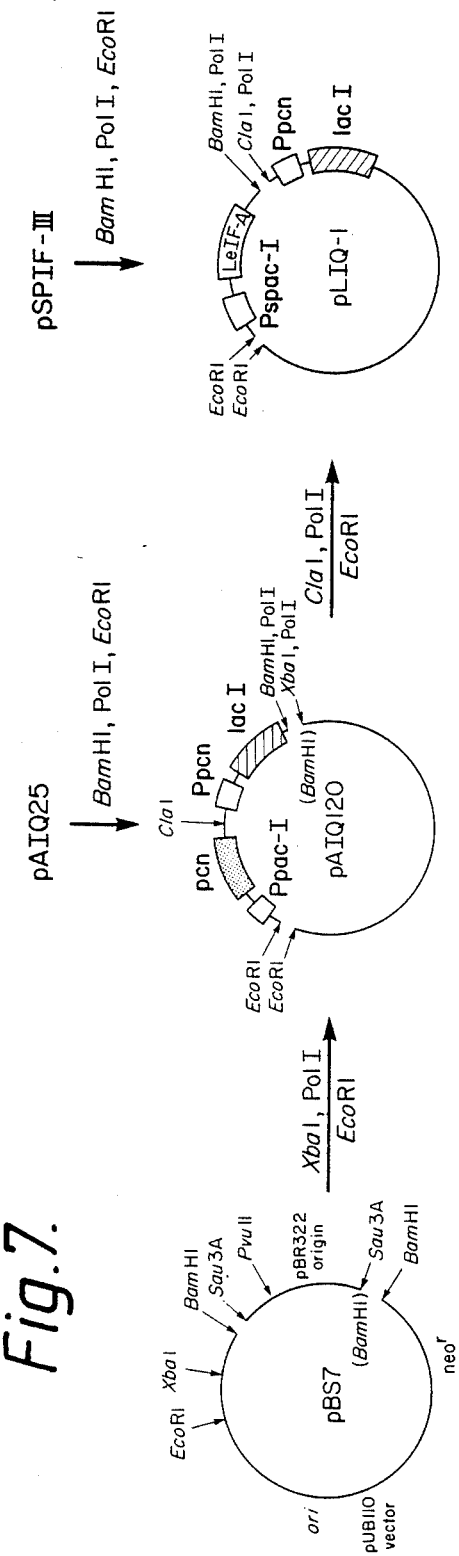
FIG. 7 shows the construction of pLIQ1, an expression vector for leukocyte interferon A under the control system of the invention, and of pAIQ120.

FIG. 7 shows the construction of pLIQ1. pLIQ1 is formed by a two way ligation of a fragment from plasmid pAIQ120 and pSPIF-III which contains the spac-1 hybrid promoter.

Plasmid pAIQ120 is analogous to the previously described plasmid pAIQ25; the major difference is that the backbone vector is a neomycin resistant plasmid. The construction of pAIQ120 is shown in FIG. 7.

The parent plasmid pBS7 is a derivative of the plasmid pUB110 described by Gryczan, T. J. et al., J. Bacteriol. 134: 318 (1978), which has been digested with BamHi, and has a partial Sau3A fragment containing the origin region of pBR322 ligated into the BamHI site. The Sau3A fragment extends from the Sau3A site at 1666 to the Sau3A site at 2332 on the standard pBR322 map (as in New England Biolabs catalogue). The BamHI site indicated in parenthesis was recreated in the ligation. pBS7 is digested with Xba1, blunt-ended with Klenow, and treated with EcoR1. The resulting fragment is ligated with the fragment resulting from BamHI digestion, blunt ending, and EcoRI digestion of pAIQ25 to give pAIQ120.

Figure 9:
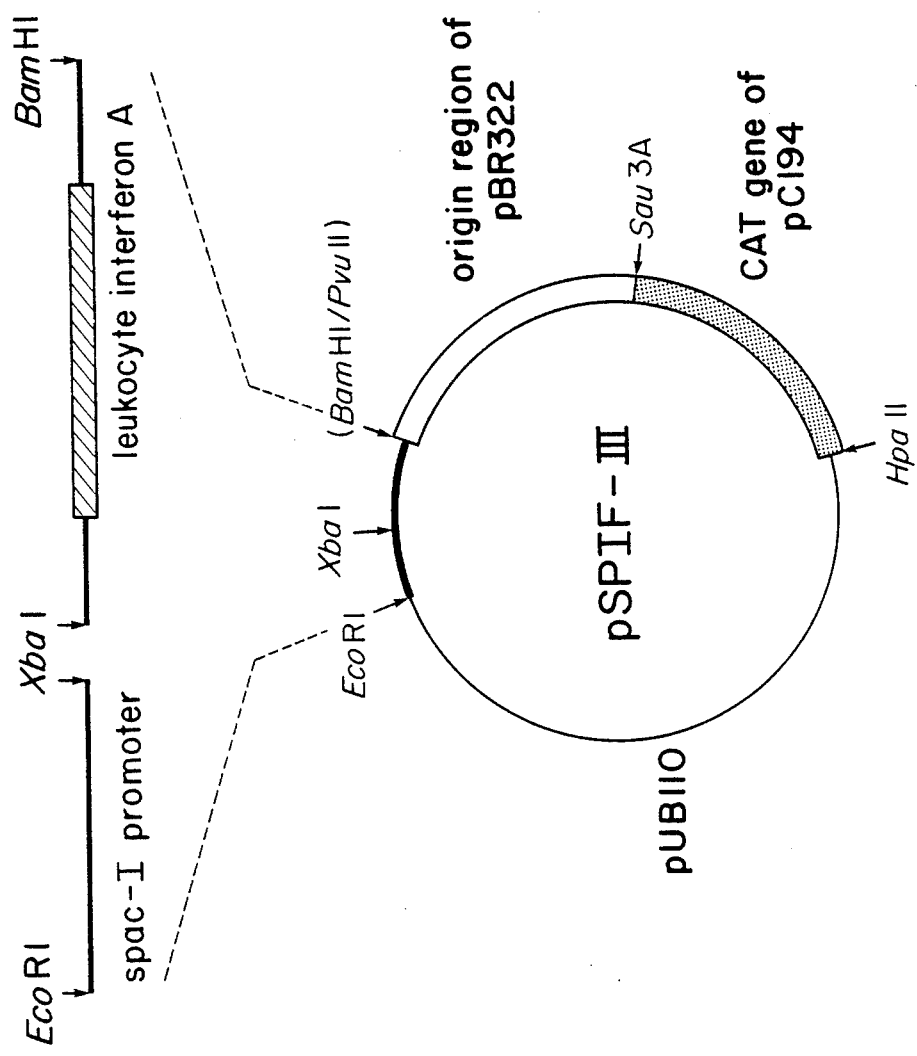
FIG. 9 shows the construction of pSPIF-III which contains the spac-1 promoter/operator operably linked to the human leukocyte interferon A gene.

The construction of pSFIF-III is shown in FIG. 9. Three fragments of DNA were ligated. The first was the spac-1 promoter from the EcoRI site to the Xbal site as indicated in FIG. 8. The second was the leukocyte interferon A gene from the XbaI site preceding the initiation codon to a BamHI site past the gene in the pBR322 vector plasmid. This fragment was isolated from a derivative of plasmid pLeIFA25 described by Goeddel et al. (1980) Nature 287: 411. This derivative has the leukocyte interferon gene placed on the pBR322 vector plasmid between the EcoRI and BamHI sites rather than between the EcoRi and PstI sites and was constructed by standard techniques. The nucleotide sequence between the XbaI site and the initiation codon of the interferon gene is identical to that of pLeIFA25 described above. The third consisted of the backbone portion of the pBS42 which has been digested with EcoRI and BamHI. To make pLIQ1, pSPIF-III is digested with BamHI blunt ended with polymerase and treated with EcoR1, and the fragment containing the leukocyte interferon gene and the spac-1 promoter isolated. Digestion of pAIQ120 with Cla 1, blunt ending with polymerase and treatment with EcoR1 provides a backbone fragment containing the lacI gene under control of the penicillinase promoter and compatible with the pSPIF-III fragment. Ligation of these fragments provides the desired plasmid, pLIQ1, as shown in FIG. 7.

D.3.2 Production of Leukocyte Interferon under Inducible Control

PLIQ1 was transformed into B. subtilis strain I168 and successful transformants were selected by neomycin resistance. Successful transformants were grown in shake flasks containing LB30 0.5 percent glucose + 10 $\mu$g/ml neomycin and in the presence or absence of 1 mM IPTG. The cultures were assayed for leukocyte interferon by the method described in paragraph C.3. Cultures grown in the presence of IPTG gave levels of interferon of 100,000 units/ml (at 10 D 600) while cultures grown in the absence of IPTG showed levels of 2000 units/ml/OD 600.

Use of constructions analogous to those in examples D.1 and D.3 substituting for penicillinase or leukocyte interferon other genes such as genus for proinsulin, or $\beta$- or $\gamma$-interferons, is well within the skill of the art. The plasmids exemplified herein may be cleaved with suitable restriction enzymes to excise the portions of DNA coding for penicillinase or leukocyte interferon A and these segments replaced by ligation with DNA fragments encoding desired proteins.

D.4 Integration of Control Sequences into the Host Genome.

D.4.1 Construction and Selection of Ery Resistant Transformants I168: ER

Figure 10:
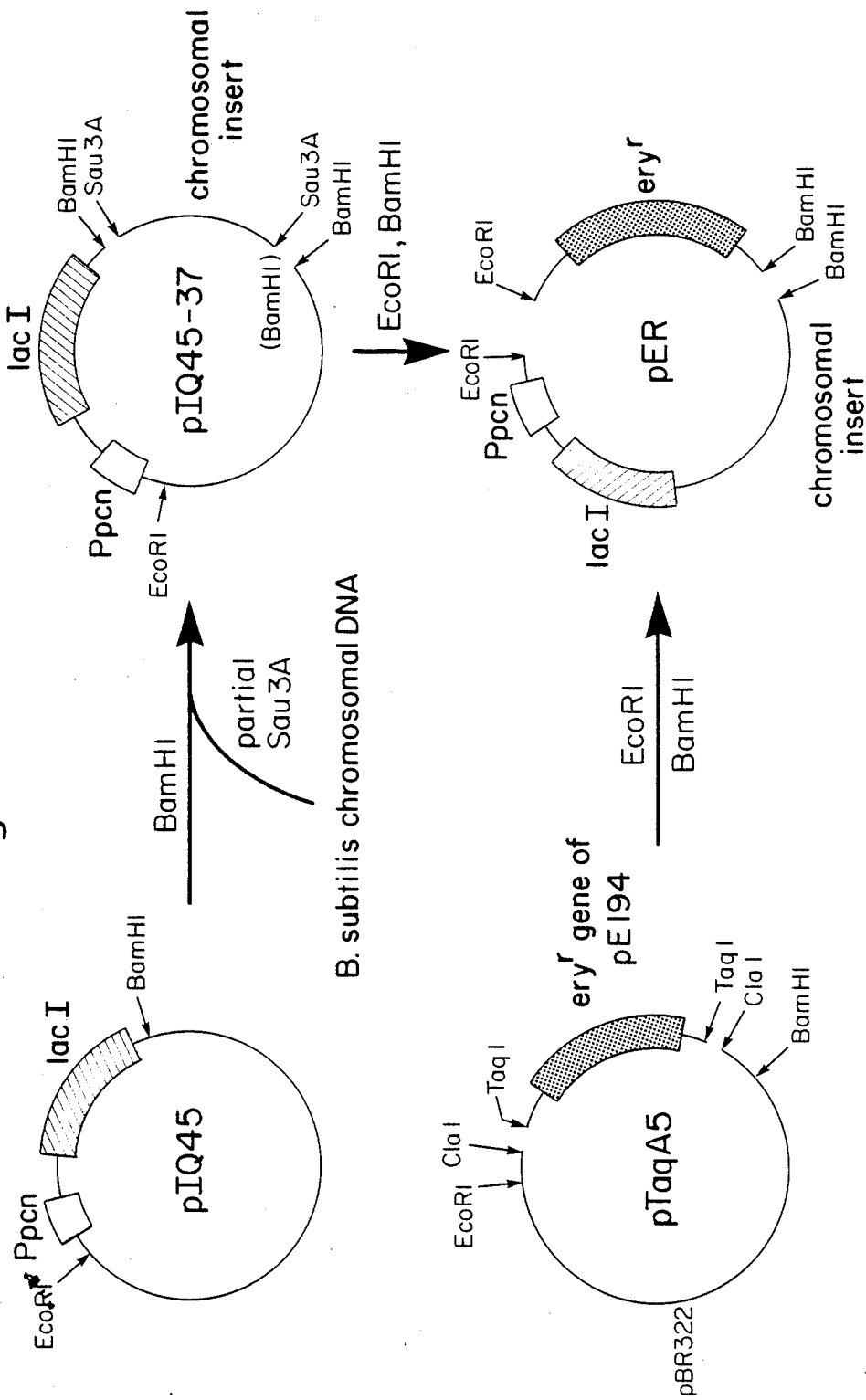
FIG. 10 shows the construction of pER which contains a chromosomal-complement insert.

The repressor plasmid pIQ45 described in D.1.3, and containing the repressor gene, was digested with BamHI and ligated with B. subtilis DNA which has been partially digested with Sau3A. B. subtilis DNA was prepared by the method of Lovett, P. S., et al, Methods in Enzymology, 68: 342 (1979), except that proteinase K was substituted for pronase. Cmp$^r$ transformants were selected and their plasmids analyzed by restriction digestion. A derivative of pIQ45 which had a Sau3A insert and a unique BamHI site on the side of the insert distal to the lac repressor gene was chosen and designated pIQ45-37 (FIG. 10).

The erythromycin resistance gene from plasmid pE194 which was described and sequenced by Horinouchi, S. and Weisblum, B. *J. Bacteriol.* 150: 804 (1982) was used as the selectable marker for introducing the lac repressor into the *B. subtilis* chromosome. In order to create useful restriction sites, the largest TaqI fragment of pE194, which contains the erythromycin resistance gene, was isolated and ligated into the ClaI site of pBR322. This derivative, called pTaqA5, contains the ery resistance gene flanked by the EcoRI and BamHI sites of pBR322.

pTAqA5 was digested with EcoRI and BamHi and the fragment containing the ery resistance gene was isolated. pIQ45-37 was also digested with EcorI and BamHI and the fragment containing the lac repressor gene and fragment of the *B. subtilis* chromosome was isolated. These two fragments were ligated and transformed into *B. subtilis* I 168.

Since neither of these two fragments contains an origin of replication, the only way that ery resistant transformants can arise is through recombination of the plasmid into the chromosome, a process previously described by Haldenwang, W. G., et. al., *J. Bacteriol.* 142: 90 (1980).

Since the lac repressor was covalently linked to the piece of chromosomal DNA needed for the integration of the ery resistance gene, all the ery resistant transformants should have the lac repressor also integrated into the chromosome. One particular ery resistant transformant was chosen and designated I168: ER.

D.4.2 Integration of the pac-I Controlled Penicillinase into I168: ER

Figure 11:
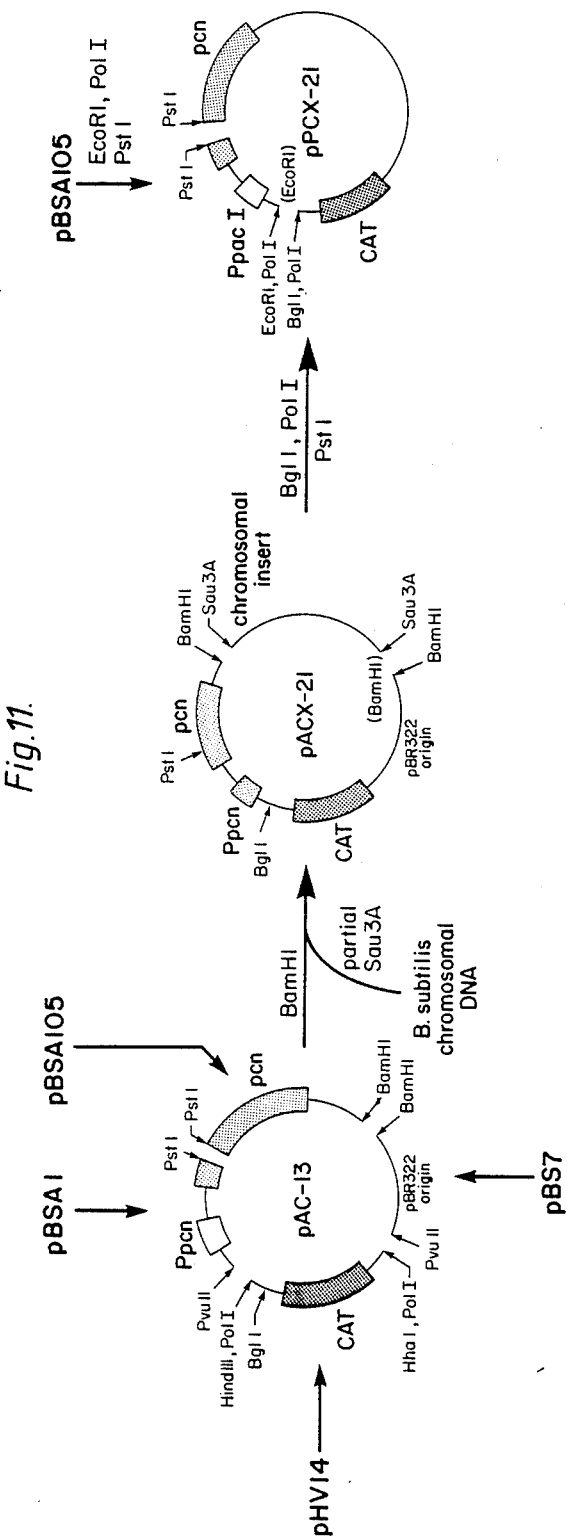
FIG. 11 shows the construction of pPCX-21 which contains the penicillinase gene under pac-1 control in an integrable plasmid.

The construction of paCX-21 carrying the pac-I controlled penicillinase gene which will integrate into the *B. subtilis* chromosome is shown in FIG. 11. The parent plasmid, pAC13, was constructed via a four fragment ligation as shown in FIG. 11.

The first PvuII-PstI fragment contains the natural penicillinase promoter and the front portion of the penicillinase gene and was derived from pBSA-1. The second Pst1-BamHI fragment contains the back portion of the penicillinase gene and is derived from pBSA-105. The third PvuII-BamHI fragment contains the pBR322 origin of replication and is derived from plasmid pBS42. The fourth HindIII-HhaI fragment contains the chloramphenicol resistance (CAT) gene from plasmid pC194 and was isolated from plasmid pHv14 described by Enrlich, S. D., *Proc. Nat. Acad. Sci.* USA 75: 1433 (1978).

In the same manner as described in the paragraph above, random Sau3A fragments of *B. subtilis* chromosomal DNA were inserted into the unique BamHI site of pAC13. One particular derivative was chosen which lacked any EcoRI, PstI or BgII sites in the random insert and was called pAcX-21 (FIG. 11).

The penicillinase gene of pACX-21 was placed under the control of the pac-I promoter by simply replacing the natural promoter with the pac-I promoter from PBSA105 to give pPCX-21 (FIG. 11).

Plasmids pPCX-21 and pACX-21 were transformed into *B. subtilis* strains I168: ER and selected for the integration of the plasmid by CMP resistance. Penicillinase assays of each plasmid integrant were performed as previously described. The results are shown below.

|         | −IPTG     | +IPTG     |
|---------|-----------|-----------|
| pACX-21 | 3500 U/ml | 3700 U/ml |
| pPCX-21 | 160 U/ml  | 3800 U/ml |

We claim:

1. A shuttle vector system for the expression of a subject DNA sequence encoding a polypeptide in a transformant bacterial host cell which comprises
   (a) a hybrid bacterial promoter/operator operably linked to the subject DNA sequence so as to effect the expression of the DNA sequence in the host cell; and
   (b) a repressor DNA sequence encoding a compatible bacterial repressor of the operator of part (a), operably linked to a promoter so as to effect expression of the repressor DNA sequence in the host cell;
   wherein the operator and the repressor are not endogenous to the host cell.

2. The shuttle vector system of claim 1 wherein the operator is the lac operator and the repressor is lacI.

3. The shuttle vector system of claim 1 wherein the subject DNA sequence encodes penicillinase or leukocyte interferon A.

4. The shuttle vector system of claim 1 wherein the promoter of parts (a) and (b) is a Bacillus promoter.

5. The shuttle vector system of claim 1 wherein the subject DNA sequence of part (a) is present on the same vector as is the repressor DNA sequence of part (b).

6. The shuttle vector system of claim 5 wherein the vector additionally contains sequences which are complementary to the host cell genome.

7. The shuttle vector system of claim 1 wherein the operator is an inducible operator.

8. The shuttle vector system of claim 1 wherein the operator and repressor are derived from a gram-negative bacterium and the host cell is a gram-positive bacterial host cell.

9. A bacterium transformed with a subject DNA sequence encoding a polypeptide, said bacterium comprising
   (a) a hybrid bacterial promoter/operator operably linked to the subject DNA sequence so as to effect the expression of the subject DNA sequence in the bacterium; and
   (b) a repressor DNA sequence encoding a compatible bacterial repressor of the operator of part (a), operably linked to a promoter so as to effect expression of the repressor DNA sequence in the bacterium;
   wherein the operator and the repressor are not endogenous to the bacterium.

10. A culture containing the bacterium of claim 9.

11. The bacterium of claim 9 which is a gram positive organism.

12. The bacterium of claim 9 wherein the subject DNA sequence of part (a) and the repressor DNA sequence of part (b) are integrated into the genome of the bacterium.

13. The bacterium of claim 9 wherein the promoter/operator of part (a) is a hybrid in which the promoter is heterologous to the operator and the operator is an inducible operator.

14. The bacterium of claim 9 wherein the operator and repressor are an *E. coli* operator and repressor, and the bacterium is non-coliform.

15. The bacterium of claim 9 that is gram positive wherein the operator and repressor are derived from a gram-negative bacterium.

16. The hybrid promoter/operator pac-1 comprising the DNA sequence of the *B. licheniformis* penicillinase promoter RNA polymerase recognition site operably linked to the operator region of the *E. coli* lac promoter/operator as to control the function of the promoter, the operator region being located 3' to the DNA sequence of the promoter RNA polymerase recognition site.

17. The hybrid promoter/operator Spac-1 comprising the DNA sequence of the SPO-1 phage promoter RNA polymerase recognition site operably linked to the operator region of the *E. coli* lac promoter/operator so as to control the function of the promoter, the operator region being located 3' to the DNA sequence of the promoter RNA polymerase recognition site.

* * * * *

UNITED STATES PATENT AND TRADEMARK OFFICE
CERTIFICATE OF CORRECTION

Page 1 of 2

PATENT NO. : 4,912,046
DATED : March 27, 1990
INVENTOR(S): Dennis J. Henner et al.

It is certified that error appears in the above - identified patent and that said Letters Patent is hereby corrected as shown below:

On Col. 3, line 5, change "induces" to --inducers--.

On Col. 3, line 63, insert --refers to a promoter-- after "promoter".

On Col. 4, line 26, change "mar." to --Mar.--.

On Col. 4, line 60, change "ia" to --is--.

On Col. 5, line 45, delete "(" before "Goeddel".

On Col. 6, line 3, change "in" to --to--.

On Col. 7, line 15, change "primary" to --primer--.

On Col. 8, line 21, insert a comma after "gene".

On Col. 9, line 3, change "pbSA80" to --pBSA80--.

On Col. 9, line 4, change "PBSA42" to --pBSA42--.

On Col. 9, line 19, change "penicilinase" to --penicillinase--.

On Col. 10, line 4, change "BstElII" to --BstEII--.

On Col. 10, line 18, change "EcorI" to --EcoRI--.

On Col. 10, line 52, change "subsubstantially" to --substantially--.

On Col. 11, line 63, change "BamHi" to --BamHI--.

On Col. 12, line 6, change "pSFIF-III" to --pSPIF-III--.

On Col. 12, line 17, change "EcoRi" to --EcoRI--.

On Col. 12, line 49, change "genus" to --genes--.

On Col. 13, line 16, change "BamHi" to --BamHI--.

On Col. 13, line 18, change "EcorI" to --EcoRI--.

On Col. 13, line 37, change "paCX-21" to --pACX-21--.

On Col. 13, line 59, change "pAcX-21" to --pACX-21--.

UNITED STATES PATENT AND TRADEMARK OFFICE
CERTIFICATE OF CORRECTION

PATENT NO. : 4,912,046
DATED : March 27, 1990
INVENTOR(S) : Dennis J. Henner et al.

It is certified that error appears in the above - identified patent and that said Letters Patent is hereby corrected as shown below:

On Col. 8, line 49, insert a comma after "A, B, and C"--.

On Col. 9, line 13, change "5'" to --3'--.

On Col. 12, line 24, insert a comma after "BamHI"--.

On Col. 13, line 52, change "Enrlich" to --Ehrlich--.

On Col. 14, line 66, change "bacterium" to --microorganism--.

On Col. 15, line 10, insert --so-- after "/operator".

Signed and Sealed this

Thirty-first Day of March, 1992

Attest:

HARRY F. MANBECK, JR.

*Attesting Officer*  *Commissioner of Patents and Trademarks*